United States Patent
Choi et al.

(10) Patent No.: US 8,491,499 B2
(45) Date of Patent: Jul. 23, 2013

(54) BIOLOGICAL FLUID SAMPLING AND PRETREATING SYSTEM AND A METHOD THEREOF

(75) Inventors: Eui Yul Choi, Gangwon-do (KR); Kie Bong Nahm, Seoul (KR); Jae Hoon Kim, Gyeonggi-do (KR); Dong Seok Jeong, Gangwon-do (KR); Sang Yeol Park, Gangwon-do (KR); Joung Dae Moon, Gangwon-do (KR); Jin Ha Jeong, Seoul (KR); Young Min Kim, Gangwon-do (KR); So Young Jung, Gangwon-do (KR); Ae Kyung Park, Seoul (KR); Byeong Chul Kim, Gangwon-do (KR)

(73) Assignee: Boditechmed Inc, Gangwon-do (KR)

( * ) Notice: Subject to any disclaimer, the term of this patent is extended or adjusted under 35 U.S.C. 154(b) by 400 days.

(21) Appl. No.: 12/742,129

(22) PCT Filed: Oct. 21, 2008

(86) PCT No.: PCT/KR2008/006223
§ 371 (c)(1),
(2), (4) Date: Aug. 2, 2010

(87) PCT Pub. No.: WO2009/064079
PCT Pub. Date: May 22, 2009

(65) Prior Publication Data
US 2010/0286557 A1    Nov. 11, 2010

(30) Foreign Application Priority Data

Nov. 12, 2007    (KR) .................. 10-2007-0115108

(51) Int. Cl.
*A61B 5/00*    (2006.01)
(52) U.S. Cl.
USPC ......................................... 600/576; 604/414

(58) Field of Classification Search
USPC ............ 600/573, 576–578; 604/414; 436/169
See application file for complete search history.

(56) References Cited

U.S. PATENT DOCUMENTS

| | | | |
|---|---|---|---|
| 5,344,417 A * | 9/1994 | Wadsworth, Jr. | 604/414 |
| 5,580,794 A * | 12/1996 | Allen | 436/169 |
| 5,833,630 A | 11/1998 | Kloth | |
| 7,378,054 B2 | 5/2008 | Karmali | |
| 2002/0188185 A1 | 12/2002 | Sohrab | |
| 2008/0167577 A1 * | 7/2008 | Weilbacher et al. | 600/576 |

FOREIGN PATENT DOCUMENTS

| | | |
|---|---|---|
| KR | 1020020094899 A | 12/2002 |
| KR | 1020050088217 A | 9/2005 |
| WO | 2004056269 A1 | 7/2004 |
| WO | 2005084545 A1 | 9/2005 |
| WO | 2005086743 A2 | 9/2005 |

* cited by examiner

*Primary Examiner* — Max Hindenburg
*Assistant Examiner* — Renee Danega
(74) *Attorney, Agent, or Firm* — Casimir Jones SC

(57) ABSTRACT

Provided is a system for sampling and pretreating biological fluid. It comprises: a piercing unit having at a lower portion a capillary tip which is to be inserted into skin to a predetermined depth to take biological fluid therethrough; a dropper, connected to an upper portion of the piercing unit, having an injection tube at an upper portion thereof, the injection tube communicating with the capillary tip; and a reagent container, designed to accommodate the piercing unit therein in an airtight manner so as to seal an outer circumference of the piercing unit, functioning to contain a reagent for treating the biological fluid of the capillary tip of the piercing unit. The system allows even a novice to sample and pretreat biological fluid with high accuracy without the use of expensive precision devices. The system employs fewer expendable supplies, thus providing higher convenience for the user.

8 Claims, 5 Drawing Sheets

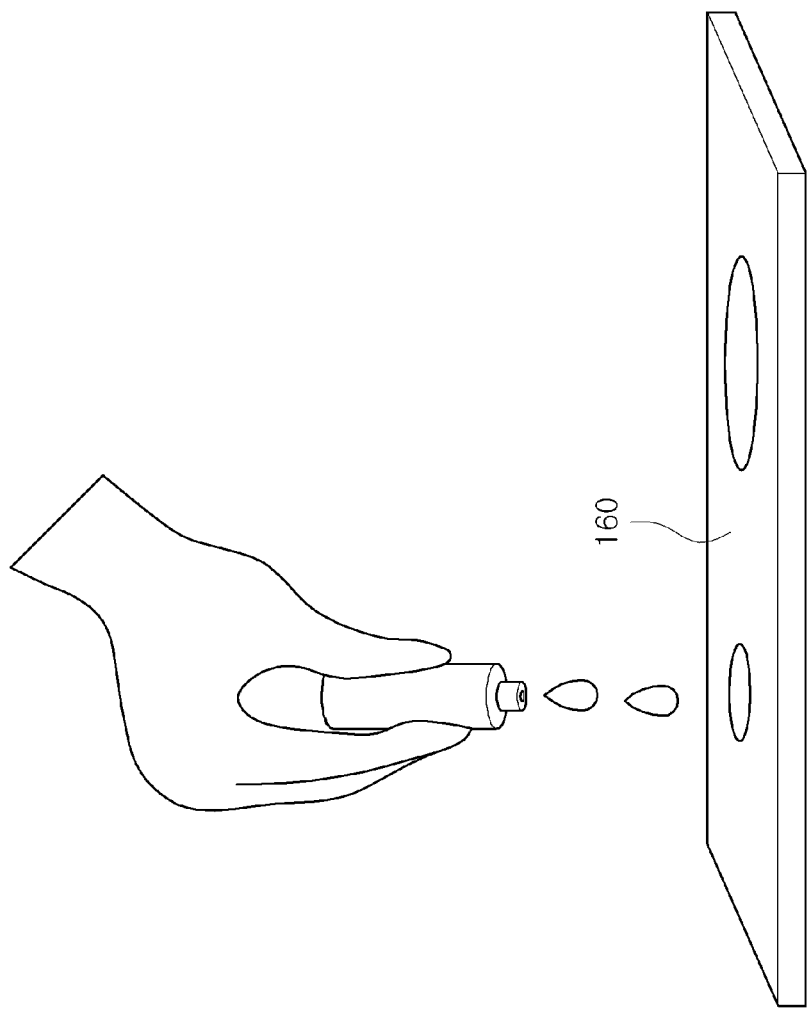

BIOLOGICAL FLUID SAMPLING AND PRETREATING SYSTEM AND A METHOD THEREOF

CROSS REFERENCE TO RELATED APPLICATIONS

The present application is a 371 of PCT/KR2008/006223 which claims priority to Korean Patent Application No. 10-2007-0115108, each of which is herein incorporated by reference in its entirety.

TECHNICAL FIELD

The present invention relates to a system and a method for sampling and pretreating biological fluid. More particularly, the present invention relates to a system and a method for sampling and pretreating biological fluid in a simpler manner.

BACKGROUND ART

Blood is one of the most useful samples in the medical diagnosis field. Generally, most analytical devices for use in diagnostic medicine are designed to react blood samples with reagents in quantitative manners and to analyze the results.

Accordingly, accurate measurements of sample quantities are physical factors which have direct influence on and make critical impact on the analytical results. Volumetric devices currently in use are precise to the microliter level and thus, measurement errors are so negligible as to have almost no effects on analytical results of samples present in milliliters.

However, when the total volume of a sample is as small as a microliter, such micro-level errors greatly affect the analysis results. For precise diagnosis with a microliter sample volume, therefore, the measurement errors must be decreased to a suitable level.

Most of the automatic precision pipetting devices developed thus far are precise enough to overcome the limitations encountered at the microliter level. However, these automatic precision pipetting devices are unsuitable for use in fields and on a small scale. The automatic devices may be economically advantageous when a great many samples are used in the laboratories. On the other hand, it is economically unfavorable to apply such an automatic device to only tens of samples. Further, the automatic devices are practically impossible to use in emergent situations.

A total volume of a microliter sample requires a measurement error of at least 0.1 μl or less in order to generate an accurate analysis result. It is very difficult to maintain an amount or volume of a sample at a constant level without a precision pipette when the quantity of the sample is very small.

Without a precision device, it is highly difficult to maintain the volumetric error within an allowable range when a sample has a total volume in the microliter range. Thus, when a sample is present in the microliter range a new technical problem arises.

In addition, after being taken in the field, a sample is pre-treated and transferred to a measurement machine in the laboratory. In the course of the sampling and transference, significant measurement error may be generated without the use of a precision pipette.

DISCLOSURE

Technical Problem

Accordingly, the present invention has been made keeping in mind the above problems occurring in the prior art, and an object of the present invention is to provide a system and a method for sampling and pretreating biological fluid by which a novice can easily sample and pretreat biological fluid samples in the microliter range with the allowance of a minimal error even after only a brief description thereof is given to the novice.

Technical Solution

In accordance with an aspect thereof, the present invention provides a system for sampling and pretreating biological fluid, comprising a piercing unit having at a lower portion a capillary tip which is to be inserted into the skin to a predetermined depth to take biological fluid therethrough; a dropper, connected to an upper portion of the piercing unit, having an injection tube at an upper portion thereof, the injection tube communicating with the capillary tip; and a reagent container, designed to accommodate the piercing unit therein in such an airtight manner as to seal an outer circumference of the piercing unit, in order to contain a reagent for treating the biological fluid of the capillary tip of the piercing unit.

In the system, the capillary tip is provided at an upper portion thereof with at least one stopper for preventing the capillary tip from being inserted into the skin in excess of a predetermined depth.

In the system, the capillary tip is provided at upper portions thereof in a circumferential direction with two or more stoppers and the outer side of each stopper 105 slants so that the width increases with the distance from the end of the capillary tip.

The stopper is provided at an upper portion thereof with a ring for connecting the stopper to the dropper.

The dropper is provided with a cylindrical member the outer circumference of which is adapted to be in airtight contact with an inner circumferential wall of the reagent container.

In the system, the injection tube is provided at a lower portion thereof with a circular plate in such a way that the circular plate is in airtight contact with an upper portion of the reagent container.

The reagent container is provided at an upper portion thereof with a sealing plate for closing the reagent container, which is designed to be readily perforated by the capillary tip of the piercing unit and to function to fill a gap between the dropper and the reagent container 120.

The dropper is provided at an upper portion thereof with a lid to which an injection tube is inserted and immobilized.

The lid is provided at an inside thereof with a groove which is flexibly relaxed when the injection tube is inserted thereto and which closes the injection tube, and the injection tube has an outer diameter which becomes upwardly narrow so that the injection tube can be easily inserted into the groove.

In accordance with another aspect thereof, the present invention provides a method for sampling and pretreating biological fluid using the system of claim 1, comprising: inserting the capillary tip into the skin to a predetermined depth to introduce a predetermined quantity of biological fluid into the capillary tip; fixedly inserting the piercing unit and a part of the dropper with the biological fluid impounded in the capillary tip into the reagent container containing a pretreatment reagent, to react the biological fluid with the reagent; and applying the pretreated biological fluid to a diagnostic kit with both the piercing unit and the dropper fixed to the reagent container.

The method may further comprise providing a dropper with a lid to which the injection tube is inserted and immobilized so as to provide a holder for the dropper.

Advantageous Effects

A system and a method for sampling and pretreating biological fluid in accordance with the present invention are so simple in operational process that even a novice can easily sample and pretreat biological fluid at the microliter scale with the allowance of a minimum of error even after only a brief description of the functioning thereof is given to the novice. Also, the present invention allows the sampling and pretreatment to be conducted with high accuracy without the use of expensive precision devices. Further, the system of the present invention employs fewer expendable supplies, thus providing higher convenience for the user.

DESCRIPTION OF DRAWINGS

FIG. 5 is a schematic view showing the application of a reaction mixture of a biological sample and a reagent to a diagnostic kit through the dropper of the system.

BEST MODE

Hereinafter, embodiments of the present invention will be described in detail with reference to the attached drawings.

Figure 1:
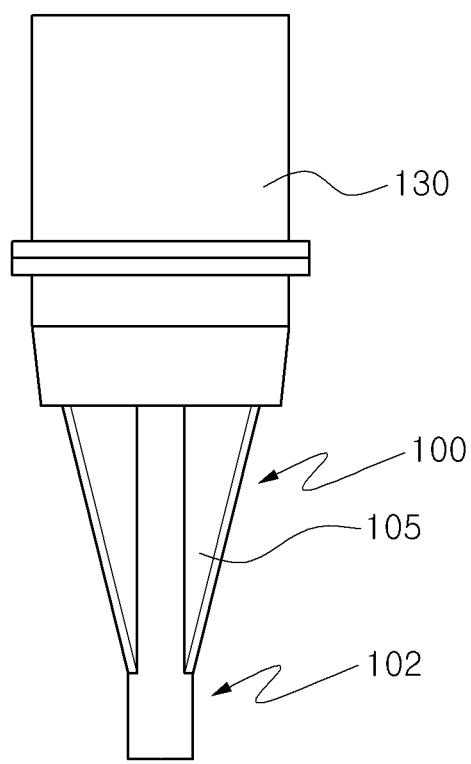
FIG. 1 is a perspective of a system for sampling and pretreating biological fluid in accordance with an embodiment of the present invention.
Figure 2:
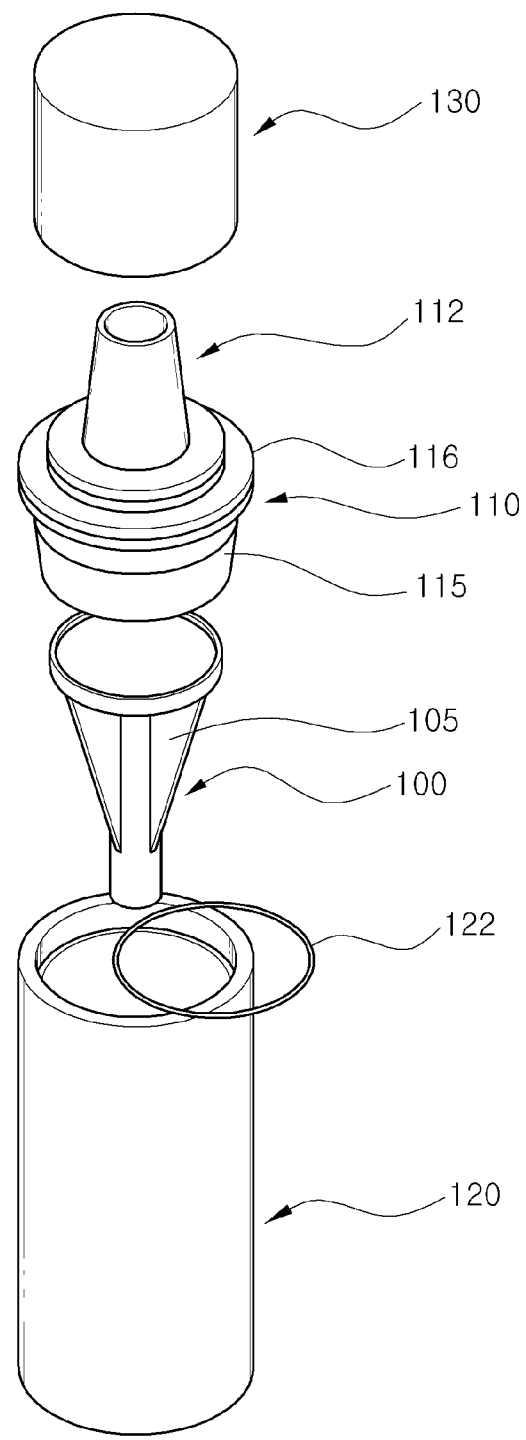
FIG. 2 is an exploded view of FIG. 1.
Figure 3:
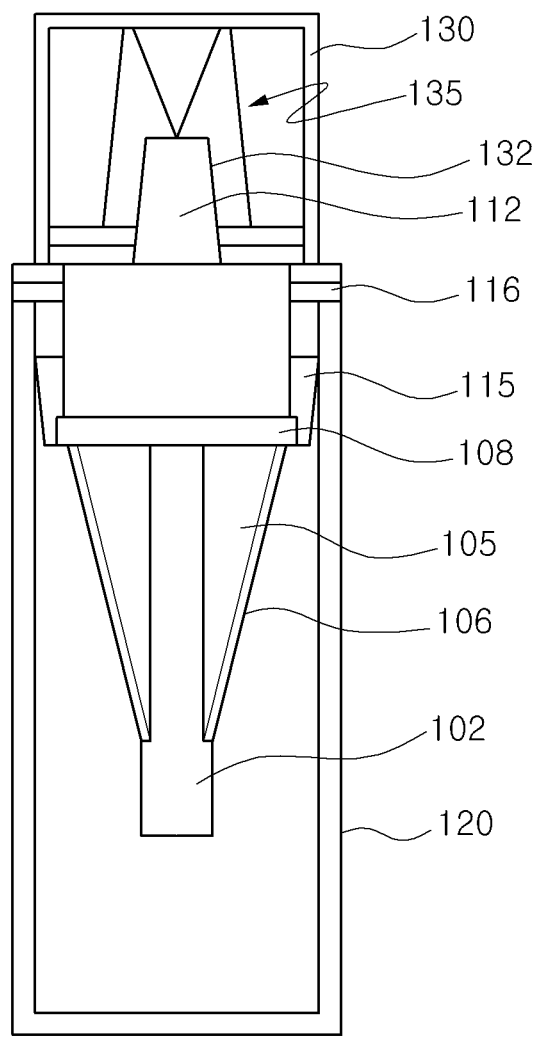
FIG. 3 is a cross-sectional view of FIG. 1.
Figure 4:
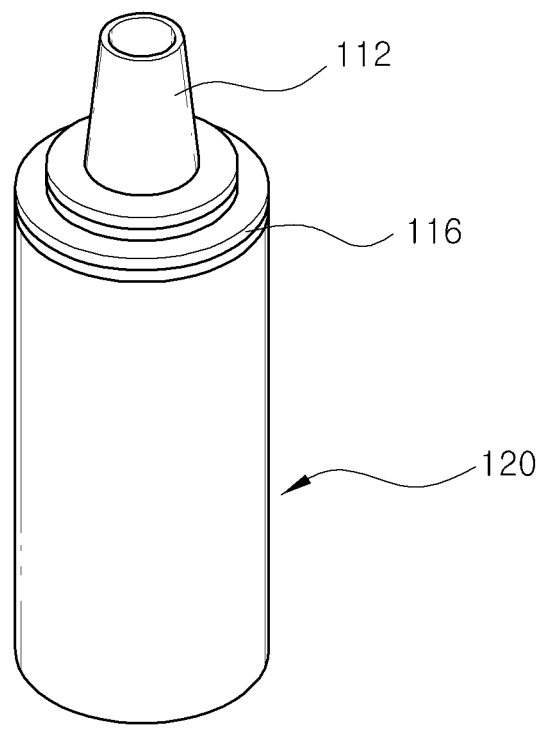
FIG. 4 is a perspective view of a reagent container of FIG. 1 into which a piercing unit is inserted.

FIG. 1 is a perspective of a system for sampling and pretreating biological fluid in accordance with an embodiment of the present invention, FIG. 2 is an exploded view of FIG. 1, FIG. 3 is a cross-sectional view of FIG. 1, FIG. 4 is a perspective view of a reagent container of FIG. 1 into which a piercing unit is inserted, and FIG. 5 is a schematic view showing the application of a reaction mixture of a biological sample and a reagent to a diagnostic kit through the dropper of the system.

With reference to FIGS. 1 and 2, the biological fluid sampling and pretreating system in accordance with an embodiment of the present invention comprises a piercing unit 100, a dropper 110 connected to an upper end of the piercing unit 100, and a reagent container 120.

The piercing unit 100 is equipped at the lower end thereof with a capillary tip 102 which pierces the skin to a predetermined depth to take biological fluid by capillary action. The dropper 110, connected to an upper end of the piercing unit 100, has an injection tube 112 at an upper portion thereof which communicates with the capillary tip 102. The reagent container 120 is provided for storing a reagent with which the sampled fluid of the capillary tip 102 is treated in advance of analysis. The reagent container 120 accommodates the piercing unit 100 in an insertion manner and is airtightly fitted to the outer circumference of the dropper 110.

The capillary tip 102 of the piercing unit 100 pierces the skin of a subject to take a biological fluid sample such as blood and is inserted into the reagent container 120 where the biological fluid sampled by the capillary tip 102 will be reacted with the reagent stored in the reagent container 120. After the outer circumference of the dropper 110 is brought into airtight contact with the inner circumference of the reagent container 120, the biological fluid is reacted with the reagent by shaking the reagent container 120.

At an upper portion of the capillary tip 102, a stopper 105 is provided for preventing the entry of the capillary tip 102 in excess of a predetermined depth into the skin. The insertion depth of the capillary can be determined by adjusting the length of the capillary tip 102 extended from the stopper 105, which determines the volume of the fluid sampled by the capillary tip 102.

A plurality of stoppers 105 may be used. In this case, the stoppers 105 are provided in a circumferential direction at upper portions of the capillary tip 102 so that the insertion depth of the capillary tip 102 may be stably maintained. The outer side of each stopper 105 slants so that its width increases with distance from the end of the capillary tip 102.

A ring 108 is provided at an upper portion of the stopper 105 to improve the binding of the stopper 105 to the dropper 110 and to prevent the stopper 105 from being broken by external force applied in a normal direction to the stopper 105.

Also, the dropper 110 is equipped with a cylindrical member 115 the outer circumference of which is adapted to be in airtight contact with the inner circumferential wall of the reagent container 120. Thus, the dropper 110 is readily immobilized to the reagent container 120 after being inserted into the reagent container 120. In this state, nothing is externally released even when the user may turn the reagent container 120 upside down. Further, a circular plate 116 may be provided at a lower portion of the injection tube 112 in such a way that it is in airtight contact with an upper portion of the reagent container 120.

Referring to FIGS. 3 and 4, a sealing plate 122 is provided on the reagent container 120 to close the reagent container 120. The reagent container 120 sealed by the sealing plate 122 safely stores and carries the reagent. When the piercing unit 100 is inserted into the reagent container 120, the sealing plate 122 is readily perforated so that the biological fluid of the piercing unit reacts with the reagent of the reagent container 120. When the reagent container 120 associated with the dropper 110 is turned upside down, the sealing plate also functions to fill a gap between the dropper 110 and the reagent container 120, thereby completely preventing the release of the reagent to the outside.

At an upper portion thereof, the dropper may be provided with a lid 130 to which the injection tube 112 is inserted and immobilized. The lid 130 is fixed to the dropper and may act as a holder of the system when the user samples a biological fluid through the capillary tip 102. Also, the lid 130 functions to protect the injection tube 112 from external impurities and impact.

Inside the lid 130 is formed a groove 130 the inner diameter of which is flexibly relaxed when the injection tube 112 is inserted thereinto. A packing is also provided inside the lid 130 to seal the injection tube 112. Hence, the injection tube 112 may have an outer diameter which becomes upwardly narrow so that it can be easily inserted into the groove 132.

In summary, the system in accordance with the present invention is operated and functions as follows: the dropper 110 is fixed to the lid 130 and acts as a holder of the system when the user takes a blood sample through the capillary tip 102; the capillary unit 102 of the piercing unit 100 is inserted into the skin to such a predetermined depth as to take a predetermined volume of the biological fluid and is then inserted into the reagent container 120 which is subsequently shaken to conduct a pre-treatment process.

Turning to FIG. 5, the method for sampling and pretreating biological fluid using the system of the present invention comprises inserting the capillary tip 102 into the skin to a predetermined depth to introduce a predetermined quantity of biological fluid into the capillary tip 102; fixedly inserting the piercing unit 100 and a part of the dropper 100 with the biological fluid impounded in the capillary tip 102 into the reagent container 120 containing a pretreatment reagent, to react the biological fluid with the reagent; and applying the pretreated biological fluid to a diagnostic kit 160 with both the piercing unit 100 and the dropper fixed to the reagent container 120.

The method may further comprise providing a dropper 110 with a lid 110 to which the injection tube 112 is inserted and immobilized so as to provide a holder of the dropper 110.

According to the method of the present invention, therefore, the sampling of biological fluid by the piercing unit 100, the pretreatment of the biological fluid with a reagent in the reagent container 120, the application of the biological fluid to the diagnostic kit 160 can be performed within one system in a batch process. Thus, the present invention allows the analysis of biological fluid to be readily conducted in a manual manner without highly expensive automatic devices.

MODE FOR INVENTION

A better understanding of the present invention may be obtained through the following examples which are set forth to illustrate, but are not to be construed as limiting the present invention.

Experimental Example 1

Measurement of Hemoglobin Level

Using the system of the present invention, hemoglobin levels were measured. Because it was made of transparent plastic, the system of the present invention could be used as a substitute for a spectrophotometer cuvette. That is, after the blood sample was mixed with the reagent, the mixture was analyzed by directly applying the system to a spectrophotometer without transferring the mixture to a spectrophotometer cuvette. After taking a small amount of whole blood (about 5 μl) therethrough, the capillary tip of the piercing unit was inserted fixedly into the reagent container containing 1 ml of a hemoglobin assaying solution and shaken to mix the whole blood with the reagent. Absorbance was measured in a spectrometer. The hemoglobin levels measured using the system of the present invention were compared to those measured using a conventional system. Eleven different hemoglobin concentrations were selected and five measurements for each concentration were represented as a mean value, along with the CV values thereof

Experimental Example 2

Volumes of Drops from the Same Dropper

In order to obtain accurate analysis results when using the system of the present invention, the drops from the dropper must be as constant in volume as possible, which is characterized by the non-pipette system according to the present invention. In this example, the drops aliquoted from the same dropper were individually measured for volume. The results are summarized in Table 2, below. As seen, differences in drop volume were not greater than expected.

TABLE 2

|  | 1 drop (μl) | 2 drops (μl) | 3 drops (μl) |
|---|---|---|---|
| Mean Vol. (20 cycles) | 39.6 | 80.1 | 119.6 |
| CV % | 3.2 | 3.2 | 3.5 |

Experimental Example 3

Volumes of Drops from Different Droppers

Drops from different droppers were measured for volume. For this, 20 different drops were used. The CV values were slightly greater or equal to those obtained when using one dropper.

TABLE 3

|  | 1 Drop (μl) | 2 Drops (μl) | 3 Drops (μl) |
|---|---|---|---|
| Mean Vol. (20 cycles) | 40.5 | 89.0 | 112.1 |
| CV % | 4.5 | 3.1 | 3.8 |

Experimental Example 4

Quantification of C-Reactive Protein with the System of the Present invention

C-reactive proteins were quantitatively measured using the system of the present invention.

In a conventional method, 5 μl of whole blood was sampled with a glass capillary tube and placed in a reaction tube containing a fluorescence-conjugate antibody after which the tube was sealed and turned upside down to discharge the blood from the capillary tube to the reaction tube. The resulting mixture was pipetted in a volume of 80 μl and loaded on a sample inlet of a diagnostic cartridge for fluorescence analysis.

In the system of the present invention, 5 μl of whole blood was taken through the capillary tip which was then inserted

TABLE 1

|  | 1 | 2 | 3 | 4 | 5 | 6 | 7 | 8 | 9 | 10 | 11 |
|---|---|---|---|---|---|---|---|---|---|---|---|
| Conventional (Mean) mg/ml | 90 | 100 | 110 | 120 | 130 | 140 | 150 | 160 | 170 | 180 | 190 |
| Inventive (Mean) mg/ml | 89 | 101 | 111 | 122 | 131 | 140 | 151 | 159 | 169 | 181 | 190 |
| Inventive (CV %) | 4.5 | 5.0 | 3.1 | 3.7 | 4.1 | 3.8 | 4.1 | 5.5 | 4.2 | 4.3 | 3.2 | into the reagent container and shaken. Subsequently, the resulting mixture was loaded through the dropper onto a diagnostic cartridge. The CV values of the results obtained using the system of the present invention, although slightly higher than those of the conventional method, were found to be good enough to be used in field examinations.

TABLE 4

Measurements of C-Reactive Protein According to Conventional Method

|  | No. of measurement | Mean Value | CV Value |
|---|---|---|---|
| Low Conc.(μg/ml) | 20 | 5.1 | 6.5 |
| Medium Conc.(μg/ml) | 20 | 51.5 | 5.2 |
| High Conc.(μg/ml) | 20 | 148.3 | 4.2 |

TABLE 5

Measurements of C-Reactive Protein According to Inventive Method

|  | No. of measurement | Mean Value | CV Value |
|---|---|---|---|
| Low Conc.(μg/ml) | 20 | 5.3 | 7.7 |
| Medium Conc.(μg/ml) | 20 | 49.8 | 5.8 |
| High Conc.(μg/ml) | 20 | 151.4 | 7.2 |

Although the preferred embodiment) of the present invention have been disclosed for illustrative purposes, those skilled in the art will appreciate that various modifications, additions and substitutions are possible, without departing from the scope and spirit of the invention as disclosed in the accompanying claims.

The invention claimed is:

1. A system for sampling and pretreating biological fluid, comprising:
   a piercing unit having at a lower portion a capillary tip which is to be inserted into skin to a predetermined depth to take biological fluid therethrough;
   a dropper, connected to an upper portion of the piercing unit, having an injection tube at an upper portion thereof, the injection tube communicating with the capillary tip; and
   a reagent container, designed to accommodate the piercing unit therein in an airtight manner so as to seal an outer circumference of the piercing unit, for containing a reagent for treating the biological fluid of the capillary tip of the piercing unit;
   wherein the dropper is provided with a cylindrical member the outer circumference of which is adapted to be in airtight contact with an inner circumferential wall of the reagent container, and the reagent container is provided at an upper portion thereof with a sealing plate for closing the reagent container, which is designed to be readily perforated by the capillary tip of the piercing unit and to function to fill a gap between the dropper and the reagent container.

2. The system according to claim 1, wherein the capillary tip is provided at an upper portion thereof with at least one stopper for preventing the capillary tip from being inserted into skin in excess of a predetermined depth.

3. The system according to claim 2, wherein the capillary tip is provided at the upper portion thereof with two or more circular stoppers.

4. The system according to claim 3, wherein the stopper is provided at an upper portion thereof with a ring for connecting the stopper to the dropper.

5. The system according to claim 1, wherein the injection tube is provided at a lower portion thereof with a circular plate in such a way that the circular plate is in airtight contact with an upper portion of the reagent container.

6. The system according to claim 1, wherein the dropper is provided at an upper portion thereof with a lid to which an injection tube is fixed.

7. The system according to claim 6, wherein the lid is provided at an inside thereof with a groove which is flexibly relaxed when the injection tube is fixed thereto and which closes the injection tube, and the injection tube has an outer diameter which becomes upwardly narrow.

8. A method for sampling and pretreating biological fluid using the device of claim 1, comprising:
   inserting the capillary tip into the skin to a predetermined depth to introduce a predetermined quantity of biological fluid into the capillary tip;
   fixedly inserting the piercing unit and a part of the dropper with the biological fluid impounded in the capillary tip into the reagent container containing a pretreatment reagent, to react the biological fluid with the reagent;
   applying the pretreated biological fluid to a diagnostic kit with both the piercing unit and the dropper fixed to the reagent container; and
   providing a dropper with a lid to which the injection tube is inserted and immobilized so as to provide a holder for the dropper.

* * * * *

UNITED STATES PATENT AND TRADEMARK OFFICE
CERTIFICATE OF CORRECTION

PATENT NO.        : 8,491,499 B2
APPLICATION NO. : 12/742129
DATED             : July 23, 2013
INVENTOR(S)       : Choi et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 323 days.

Signed and Sealed this
Eighth Day of September, 2015

Michelle K. Lee
*Director of the United States Patent and Trademark Office*